US00PP21754P2

(12) United States Plant Patent
Verschoor

(10) Patent No.: US PP21,754 P2
(45) Date of Patent: Mar. 1, 2011

(54) ***PHLOX* PLANT NAMED 'NEON FLARE'**

(50) Latin Name: *Phlox paniculata*
Varietal Denomination: Neon Flare

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 12/592,149

(22) Filed: Nov. 19, 2009

(51) Int. Cl.
*A01H 5/00* (2006.01)

(52) U.S. Cl. ..... Plt./320
(58) Field of Classification Search ..... Plt./320
See application file for complete search history.

*Primary Examiner*—June Hwu
(74) *Attorney, Agent, or Firm*—Audrey Charles

(57) ABSTRACT

A new and distinct cultivar of *Phlox* plant named 'Neon Flare', particularly distinguished by white and magenta bicolored flowers, compact habit, healthy foliage, and good mildew resistance, is disclosed.

2 Drawing Sheets

Latin name of genus and species of plant claimed: *Phlox paniculata.*

Variety denomination: 'Neon Flare'.

BACKGROUND OF THE INVENTION

The present invention relates to a new and distinct cultivar of *Phlox* plant botanically known as *Phlox paniculata* and hereinafter referred to by the cultivar name 'Neon Flare'. The new cultivar originated from an open pollination in 2005 in a nursery location in Haarlem, The Netherlands between unknown male and female *Phlox paniculata* plants.

The new cultivar was selected from the results of the open pollination in 2006 in Haarlem, The Netherlands. Asexual reproduction of the new *Phlox* by vegetative cuttings in a controlled environment in Haarlem, The Netherlands since the summer of 2006, has shown that the unique features of the *Phlox* are stable and reproduced true to type in successive generations.

SUMMARY OF THE INVENTION

The following are the most outstanding and distinguishing characteristics of this new cultivar when grown under normal horticultural practices in Haarlem, The Netherlands:

1. White and magenta bicolored flowers;
2. Compact habit;
3. Healthy foliage; and
4. Good mildew resistance.

Of the many commercially available *Phlox* cultivars, the most similar in comparison to the new cultivar is 'Windsor', not patented. However, in side by side comparisons in Haarlem, The Netherlands, plants of the new cultivar 'Neon Flare' differ from plants of 'Windsor' by having healthier foliage, thicker stems, and a sturdier, more compact plant habit. Additionally, 'Neon Flare' flowers more evenly with flowers that have a richer color than those of 'Windsor'.

In addition, plants of the new cultivar 'Neon Flare' are similar to 'Strawberry Daiquiri', U.S. Plant Pat. No. 20,801. However, in side by side comparisons in Haarlem, The Netherlands, plants of the new cultivar 'Neon Flare' differ from plants of 'Strawberry Daiquiri' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Neon Flare'. The plant was field grown for approximately 1 year in Haarlem, The Netherlands in an outdoor nursery location.

DETAILED BOTANICAL DESCRIPTION

Figure 1:
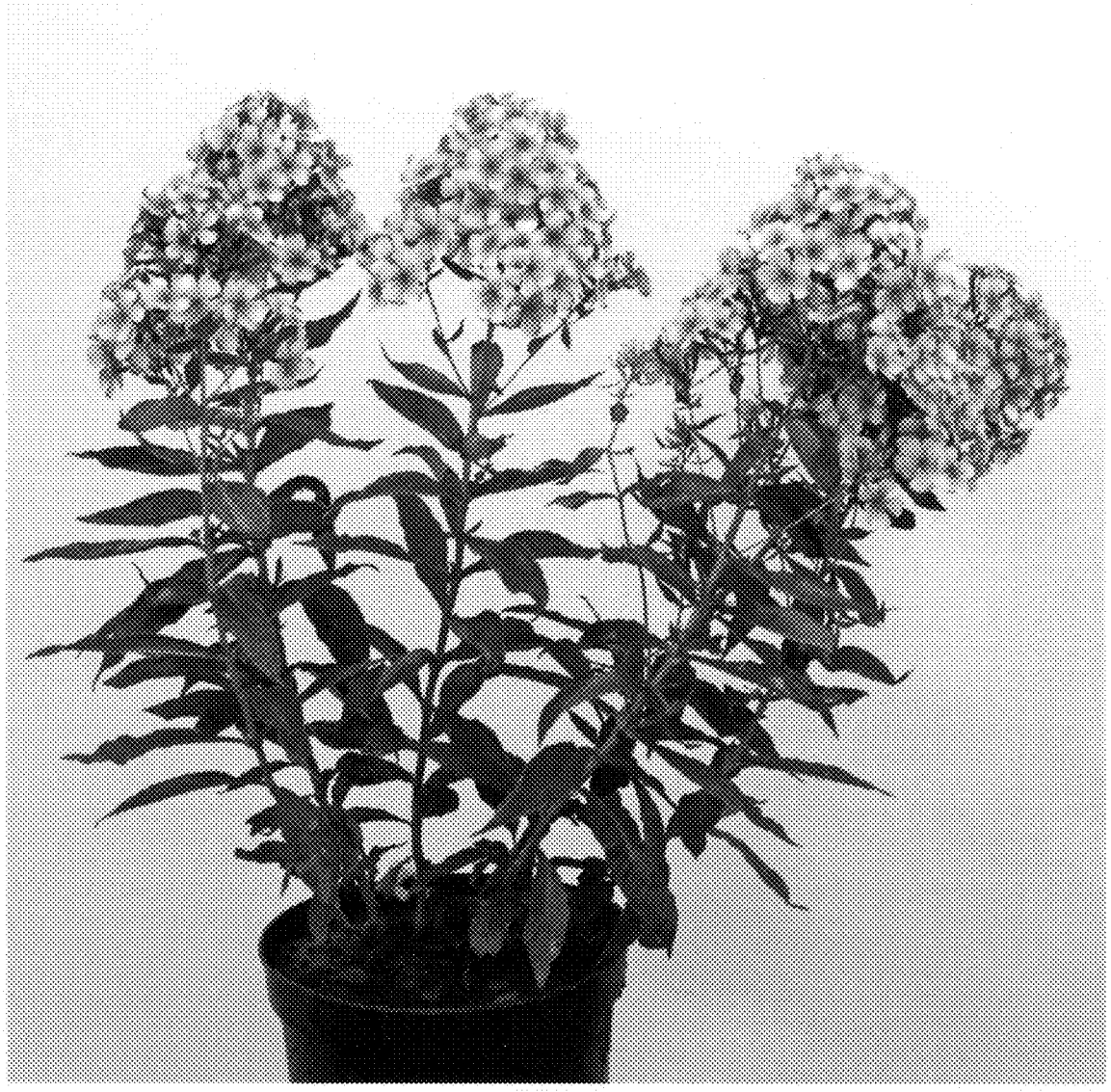
FIG. 1 illustrates a side view of the overall growth and flowering habit of 'Neon Flare'.
Figure 2:
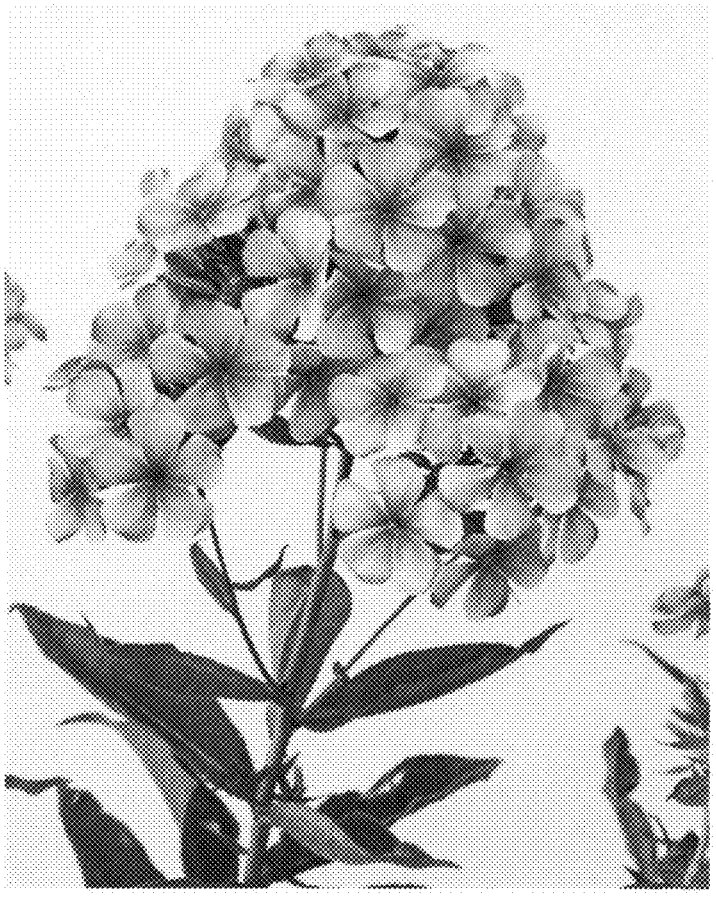
FIG. 2 illustrates a close-up view of an individual inflorescence of 'Neon Flare'.
Figure 3:
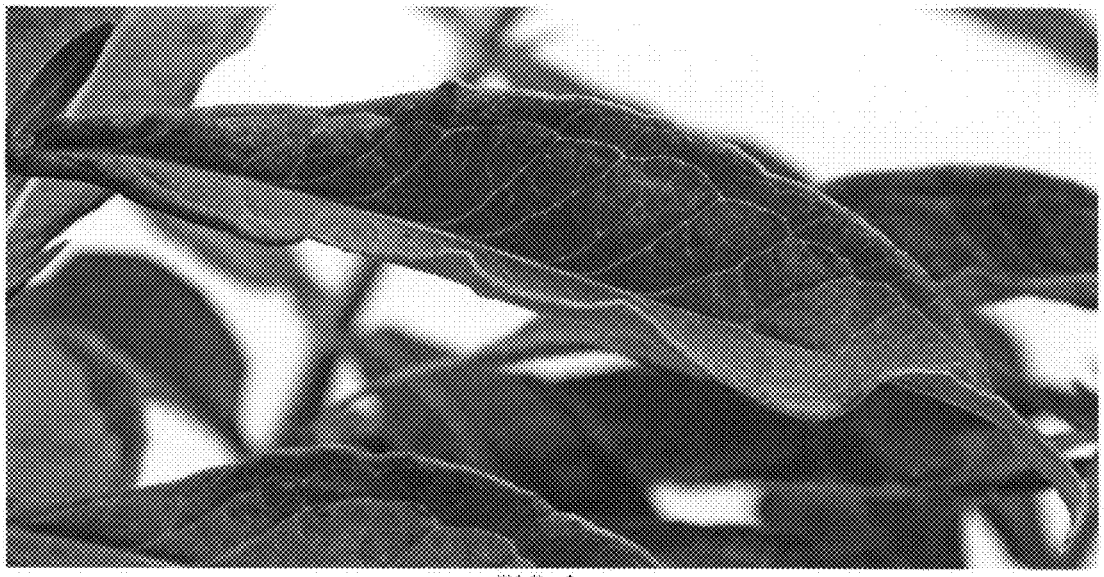
FIG. 3 illustrates a close-up view of the foliage of 'Neon Flare'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Haarlem, The Netherlands. The plant history was taken in August 2009 on 1-year-old field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Phlox paniculata* cultivar 'Neon Flare'.

Parentage:

*Female parent.*—Unknown *Phlox paniculata.*

*Male parent.*—Unknown *Phlox paniculata.*

Propagation:

*Type cutting.*—Vegetative cutting.

*Time to produce a rooted cutting.*—Approximately 30 days with average soil temperature of 21° C.

*Root description.*—White, thin, fibrous, sparse.

*Rooting habit.*—Freely branching.

Plant description:

*Type.*—Herbaceous perennial. Overall shape: Narrow inverted triangle. High temperature tolerance: Tolerant to at least 35° C. Low temperature tolerance: Hardy to at least USDA Zone 4. Excellent garden performance.

*Commercial crop time.*—Approximately 25 weeks from rooted cutting to finish in a 1.5 liter container.

*Growth habit and general appearance.*—Upright, moderately vigorous.

*Size.*—Height from soil level to top of plant plane: Approximately 47.8 cm. Width: Approximately 43.1 cm. Rate of growth: In spring, approximately 7 cm per month.

*Branching habit.*—Low to moderate basal branching; pinching will improve basal branching; flowering stems grow from base. Quantity of branches per plant: Approximately 6 flowering stems.

*Stem.*—Shape: Rounded. Strength: Strong. Aspect: Erect. Length to base of inflorescence: Approximately 29.5 cm. Diameter: Approximately 4.0 mm. Length of central internode: Approximately 2.3 cm. Texture: Glabrous, slightly glossy. Color of young and mature stems: 144B.

Foliage description:

*General description.*—Quantity of leaves per stem: Approximately 26. Form: Simple. Arrangement: Opposite. Durability to stress: High.

*Leaves.*—Shape: Narrowly ovate to narrowly elliptic. Margin: Slightly revolute, very short and finely serrate with approximately 30 teeth per cm. Apex: Narrowly acute. Base: Truncate. Venation pattern: Pinnate. Length of mature leaf: Approximately 10.1 cm. Width of mature leaf: Approximately 3.0 cm. Texture of upper and lower surfaces: Smooth, glabrous. Color of upper surface of young foliage: 137B with venation of 144C to 144D. Color of lower surface of young foliage: 138A to 138B with venation of 144D. Color of upper surface of mature foliage: 137A with venation of 144C to 144D. Color of lower surface of mature foliage: 147B with venation of 144D.

*Petiole.*—Shape: V-shaped. Length: Approximately 3.0 mm. Width: Approximately 3.0 mm. Height: Approximately 3.0 mm. Color: 144C.

Flowering description:

*Flowering habit.*—Freely flowering under outdoor growing conditions with substantially continuous blooming from summer through late summer.

*Lastingness of flower on the plant.*—Approximately 10 days.

*Flowering response time.*—Approximately 60 days.

Inflorescence description:

*General description.*—Type: Compound terminal panicle, self-cleaning. Fragrance: Moderately, sweet and pleasant; typical *Phlox paniculata* scent. Height: Approximately 17.2 cm. Width: Approximately 15.0 cm. Quantity of opened flowers per inflorescence: Approximately 200. Rate of flower opening: Approximately 20% of the flowers at any stage.

*Peduncle.*—Strength: Strong. Aspect: Erect primary peduncles with secondary peduncles at approximately a 45° angle. Length of primary: Approximately 13.9 cm. Diameter of primary: Approximately 2.5 mm. Length of secondary: Approximately 4.5 cm. Diameter of secondary: Approximately 1.0 mm. Texture: Smooth, glabrous. Color: 144A to 144B.

Flower description:

*General description.*—Type: Single. Shape: Salverform. Aspect: Upright to outward.

*Bud just before opening.*—Quantity per inflorescence: Approximately 100. Shape: Oblanceolate. Length: Approximately 1.4 cm. Diameter: Approximately 4.0 mm. Color: Petals of 72B; calyx base of 147D transitioning to 147A toward apex. Rate of opening: Approximately 4 days.

*Corolla.*—Depth: Approximately 2.1 cm. Diameter: Approximately 2.8 cm.

*Petals.*—Quantity: 5, lower 55% of each petal fused into a narrow tube. Arrangement: Rotate. Appearance: Dull. Shape, lobe: Spathulate. Margin: Entire. Apex: Broadly rounded. Length: Approximately 3.0 cm. Length of free portion: Approximately 1.3 cm. Width: Approximately 1.3 cm. Texture of upper and lower surfaces: Smooth. Color of upper surface when first open: Pure white with an overlay of N74A through N74D, overlay is darkest at upper left margin and nearest tube opening, tube of N77D. Color of lower surface when first open: 76D with 77B to 77C, tube of N77C to N77D. Color of upper surface when fully open: Pure white with an overlay of N74A through N74D, overlay is darkest at upper left margin and nearest tube opening, tube of N77D. Color of lower surface when fully open: 76D to 77C, tube of N77C to N77D.

*Calyx.*—Shape: Campanulate. Length: Approximately 9.0 mm. Diameter: Approximately 3.0 mm.

*Sepals.*—Quantity: 5, lower fifth fused into a narrow tube. Arrangement: In a single whorl. Appearance: Moderately glossy. Shape: Linear. Margin: Entire. Apex: Narrow apiculate. Length: Approximately 9.0 mm. Width: Approximately 1.3 mm. Texture of upper and lower surfaces: Smooth, moderately glossy. Color of upper and lower surfaces of immature sepals: 147A with margins and base of 144B to 147D. Color of upper and lower surfaces of mature sepals: 147A with margins and base of 144B to 147D.

*Pedicel.*—Strength: Strong. Aspect: Erect when directly adjoining peduncle, others at an approximately 60° angle. Length: Approximately 8.0 mm. Diameter: Approximately 1.0 mm. Texture: Smooth, glabrous. Color: 144A to 144B.

*Reproductive organs.*—Androecium: Stamen quantity: 5 per flower, basifixed. Anther shape: Oblong. Anther length: Approximately 1.5 mm. Filament length: Approximately 1.0 mm. Anther color: 22A. Pollen amount: Sparse. Pollen color: 11C to 11D. Gynoecium: Pistil quantity: 1 per flower. Pistil length: Approximately 1.8 cm. Stigma shape: Cleft (3-parted). Stigma color: 150D. Style length: Approximately 1.6 cm. Style color: N77D and lighter. Ovary color: 143A.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Phlox* plant named 'Neon Flare', substantially as herein shown and described.

* * * * *